United States Patent [19]

Brown et al.

[11] Patent Number: 4,694,692

[45] Date of Patent: Sep. 22, 1987

[54] DRILLING FLUID DENSITY MEASUREMENT SYSTEM

[75] Inventors: Gregory D. Brown; Darrel E. Clark; Rodger W. Schuermann, all of Norman, Okla.

[73] Assignee: Technical Oil Tools Corporation, Norman, Okla.

[21] Appl. No.: 870,343

[22] Filed: Jun. 4, 1986

[51] Int. Cl.[4] .......................... G01N 9/28; E21B 47/00
[52] U.S. Cl. ........................................ 73/155; 73/439; 73/153
[58] Field of Search ............... 73/151, 153, 155, 438, 73/439, 299, 302, 4 R; 175/48; 364/422, 558

[56] References Cited

U.S. PATENT DOCUMENTS

| | | | |
|---|---|---|---|
| 2,373,795 | 4/1945 | Warren, Jr. | 73/439 |
| 2,604,778 | 7/1952 | Marquardt | 73/439 |
| 3,460,394 | 8/1969 | Cryer | 73/439 |
| 3,780,581 | 12/1973 | Acre et al. | 73/302 |
| 3,911,741 | 10/1975 | Rochon et al. | 73/153 |
| 4,006,635 | 2/1977 | Khol | 73/302 |
| 4,043,193 | 8/1977 | Bailey | 73/155 |
| 4,201,082 | 5/1980 | Dockhorn et al. | 73/153 |
| 4,393,705 | 7/1983 | Eldschun | 73/439 |
| 4,408,486 | 10/1983 | Rochon et al. | 73/155 |
| 4,576,035 | 3/1986 | Hooven et al. | 73/4 R |

Primary Examiner—Stewart J. Levy
Assistant Examiner—Scott M. Oldham
Attorney, Agent, or Firm—Norvell & Associates

[57] ABSTRACT

A drilling fluid density measurement system uses a continuously operating bubble measurement system for an oil or gas well. A microprocessor correlates the signal output from a differential pressure transmitter connected to a pair of self-cleaning pressure probes which are positioned in a circulating drilling fluid. By manipulating solenoid valves, the microprocessor controls the intermittent zeroing of the output signal from the differential pressure transmitter and controls a periodic level check to determine if the pressure probes are submerged in the drilling fluid.

15 Claims, 8 Drawing Figures

DRILLING FLUID DENSITY MEASUREMENT SYSTEM

BACKGROUND OF THE INVENTION

1. Field of the Invention

This invention relates to a continuous drilling fluid density measurement system and apparatus for use in a drilling fluid injection system in a subterranean oil or gas well.

2. Description of the Prior Art

The utilization of air bubble probes for monitoring the density of fluids is a technique that has long been practiced. Two such probes are employed and are inserted in the fluid at two different depths so that a pressure opposing the flow of bubbles from each of the two probes is produced on the probes which is proportional to the density of the fluid. Air bubbles are then forced through the probes and out the bottom ends thereof at a constant rate, and the pressure required to produce such constant flow through each of the two tubes is measured. The differential in such pressures is multiplied by a scaling factor to yield the density of the fluid.

This technique is quite satisfactory for use with clean process fluids which do not collect or congeal around the passageway through which the air bubbles are emitted. A sufficient constriction of the air bubble passageway obviously results in a higher pressure being required to maintain the constant flow of bubbles required for the measuring technique. Thus, the increased pressure would result in an erroneous mud density determination.

By their very nature, drilling fluids or drilling mud differ significantly from clean processed fluids because the drilling fluids are intended to collect or congeal in small passageways, such as the passageways through which air bubbles are emitted in a differential pressure density-measuring device. A conventional drilling fluid or drilling mud contains fine particles of clay in suspension which enter and accumulate in crevices and pores in the well bore during circulation of the drilling fluids as part of a rotary drilling operation. The clay in suspension is intended to gel and eventually close the opening through the wall rocks in the well bore to seal the openings against movement of fluid either from or into the well bore.

Mud weight or density-measuring devices using the technique of measuring the differential pressure between two vertically spaced points in a predetermined volume of fluid had been used in conjunction with drilling operations. One such device periodically collects a mud sample having a specified volume. After the weight of each constant volume sample is determined by the differential pressure method, the fluid sample is completely flushed out of the test container before a new, fresh sample is collected through the use of a vacuum. The flushing action permits the instrument to accurately handle foamy mud or mud containing lost circulation materials. This mud-weighing system involves the intermittent sampling and weighing of the drilling fluid, and mud does not stand stagnant in the weighing unit resulting in a false weight recording. See Rogers, *Composition and Properties of Oil Well Drilling Fluids;* Gulf Publishing Company, 1963, pp. 65–67.

Drilling fluids or drilling mud is circulated through the well bore during a rotary drilling operation. This drilling fluid is used to carry drill cuttings from the bottom of the well to the surface, to lubricate the rotating drill pipe, and to close the pores of formations yielding high-pressure gas or water. Drilling fluid is also used to seal permeable low-pressure formations, fissures, or crevices through which the drilling fluid might otherwise circulate.

Drilling fluid must also have a sufficient density to provide hydrostatic pressure to prevent high-pressure gas, oil, or water from entering the well in a sufficient quantity and rate to cause a blowout. If a high-pressure gas is encountered during drilling, the density of the "gas-cut" drilling fluid, containing entrained gas bubbles is reduced, perhaps to such an extent as to permit a sudden flow of high-pressure gas to enter the well and violently eject the drilling fluid. The density of the drilling fluid is critical in maintaining an opposing hydrostatic pressure to prevent extraneous fluids or gases from entering the well. For example, drilling fluids weighing 70 or 75 pounds per cu. ft. will ordinarily be sufficient to control formation fluids, but when high-fluid pressures are encountered, heavier drilling fluids must be employed. Hydrostatic pressures of about 0.7 psi per ft. may become necessary to maintain adequate hydrostatic pressure.

The density of the drilling fluid can be significantly reduced when gas is occluded in the drilling fluid. When sufficient gas is entrained in the fluid to seriously reduce the density, the differential pressure between the formation and the well is increased and additional gas can enter the well. The volume of gas in the material will also expand at lower pressures contributing to a loss in drilling fluid density.

Drilling fluid or drilling mud comprises a special mixture of clay, water, and chemical additives, pumped downhole through the drill pipe and drill bit. The mud cools and lubricates the drill bit and drill pipe and carries rock cuttings to the surface. The mud serves as a plaster to prevent the wall of the borehole from crumbling or collapsing. Drilling mud also provides the weight or hydrostatic head to prevent extraneous fluids, such as natural gas, from entering the well bore to cause a potential blowout. Among the properties of clay-laden fluids that are important in determining their performance as circulating fluids or muds in rotary drilling are: density, viscosity, colloidity, sheer or gel strength, and sand and salt content. The density of a drilling fluid depends upon the amount and specific gravity of the suspended solids therein. Clay-laden fluids of density and viscosity suitable for rotary drilling purposes range in weight from 8.0 to 24 pounds per gallon and have equivalent specific gravities of 0.96 to 2.88. Drilling fluid or mud weight is measured by the pressure developed by the fluid in pounds per square inch per hundred feet of depth.

SUMMARY OF THE INVENTION

A drilling fluid density measurement system comprises pneumatic and electrical components including a microprocessor for determining the density of the drilling fluid in a reservoir such as a mud pit by bubbling air or another gas through the drilling fluid. Two pressure probes are submerged within the drilling fluid at different depths. Air or gas is bubbled through a nozzle at the end of each tubular pressure probe at a constant rate determined by a flow regulator. When a constant rate of flow is established in each probe, the difference in pressures required for the two probes to achieve a constant rate of air flow is directly proportional to the density of the drilling fluid. A microprocessor can be employed to correlate the pressure signal from the pressure probes with the density of the mud by application of an appropriate scaling factor. The two pressure probes are in communication with a differential pressure transmitter which emits an output signal proportional to the difference in pressure between the two probes and proportional to the density of the drilling fluid. A valve is used to input pressure from the same pressure probe on opposite sides of the differential pressure transmitter to create a zero differential pressure. The output of the differential transmitter under the zero differential condition is monitored by the microprocesser to intermittently account for the drift in the zero value of the differential pressure transmitter. Level check means in which a negative pressure is generated by disconnecting the high-pressure probe is also provided. If atmospheric pressure is sensed on both the high- and low-pressure sides of the differential pressure transmitter, it follows that the upper pressure probe is no longer submerged within the drilling fluid thus indicating that the level is too low for the pressure differential between the upper and lower probes to correspond to the density of the drilling fluid. Select valves are also provided for using a single differential pressure transmitter to selectively measure the drilling fluid density in a plurality of drilling fluid reservoirs such as the mud pit or possum belly immediately downstream of the exit of the drilling fluid from the well bore and the suction pit upstream of the entrance of the drilling fluid into the well bore. Additionally, the microprocessor periodically actuates a probe cleaning plunger of the type disclosed in our copending application Ser. No. 919,010, filed Oct. 15, 1986.

BRIEF DESCRIPTION OF THE DRAWINGS

In FIG. 3 the density of the drilling fluid in the tank adjacent the exit of the drilling fluid from the well bore is being measured.

DETAILED DESCRIPTION OF THE PREFERRED EMBODIMENT

Figure 1:
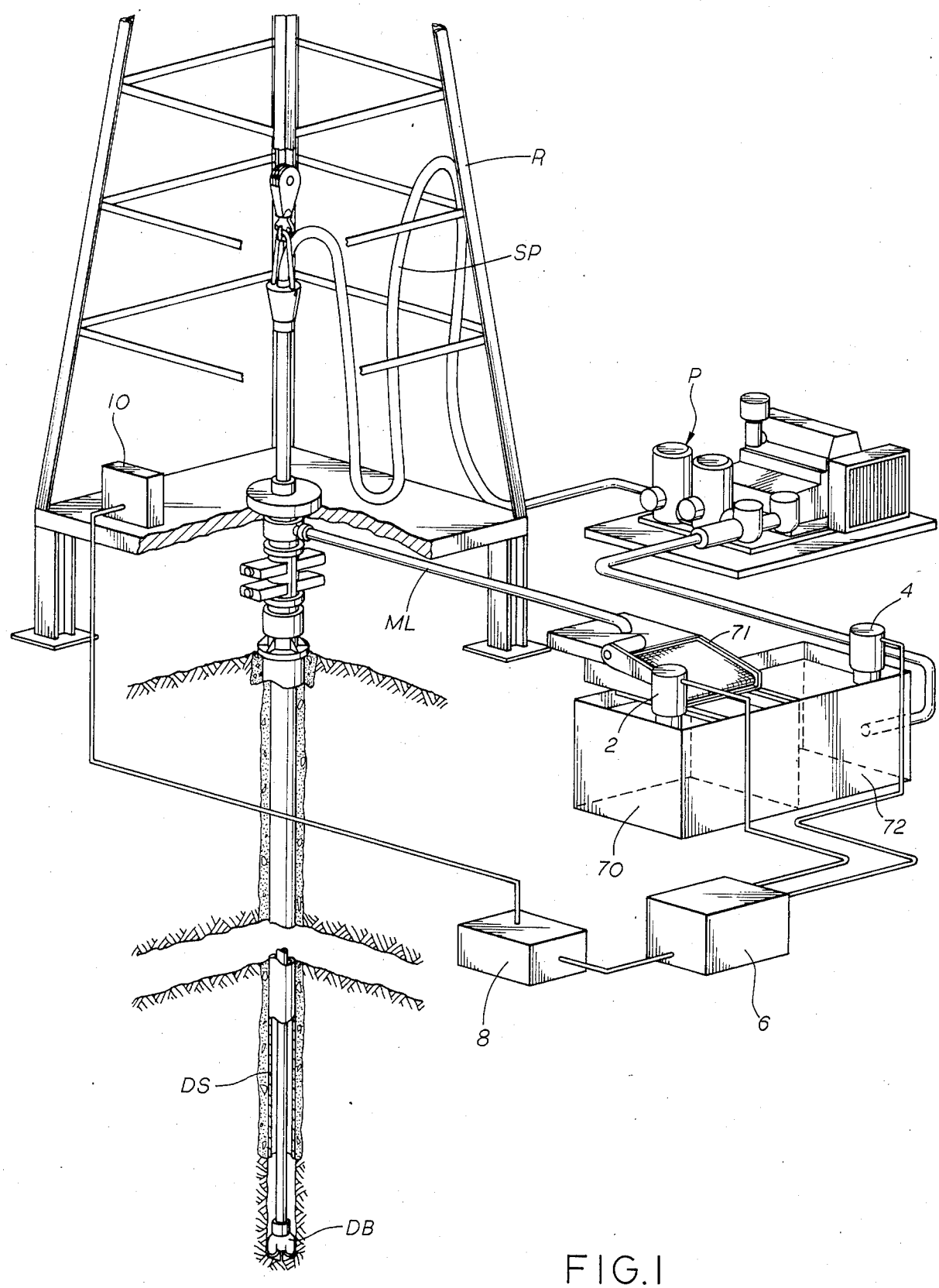
FIG. 1 is a cutaway view illustrating the circulation of a drilling fluid between surface tanks and into a well bore as a well bore is drilled.

The mud density measurement system described herein is especially adapted for use in a conventional rotary drilling operation in which drilling fluid is circulated into and from the well bore as the well is drilled. FIG. 1 illustrates a conventional circulating drilling fluid system with which the mud density measuring system comprising probe set assemblies 2 and 4, pneumatic subassembly 6, electronic subassembly 8, and remote display subassembly 10 can be employed. As the rotary drill bit DB advances in the well bore, drilling fluid is circulating through a drill string DS through the bit and up the annulus around the exterior of the drill string to the surface. This drilling fluid removes drill bit cuttings, lubricates the drill bit and the drill string, and contains materials disbursed therein to seal crevices and pores in the wall of the well bore. As the drilling fluid exits the well bore at the surface, it is deposited in a reservoir, tank, or possum belly 70. The drilling fluid is then transferred across a shale shaker 71 to remove cuttings, to a separate tank or suction pit 72 adjacent the well bore entrance of the circulating path. The drilling fluid may be replenished at the surface to replace fluids lost to subsurface formations and suitable treatment materials may be added to the drilling fluid at the surface. The pump P then pumps the drilling fluid or drilling mud from the suction pit 72 into the drill string DS through stand pipe SP located on the drilling rig R. It will be, of course, understood by those skilled in the art that FIG. 1 is merely representative of a conventional circulating drilling fluid system. The drilling fluid density measurement system disclosed herein can be employed with this conventional system and with other conventional drilling fluid systems whether, circulating or not.

Figure 2:
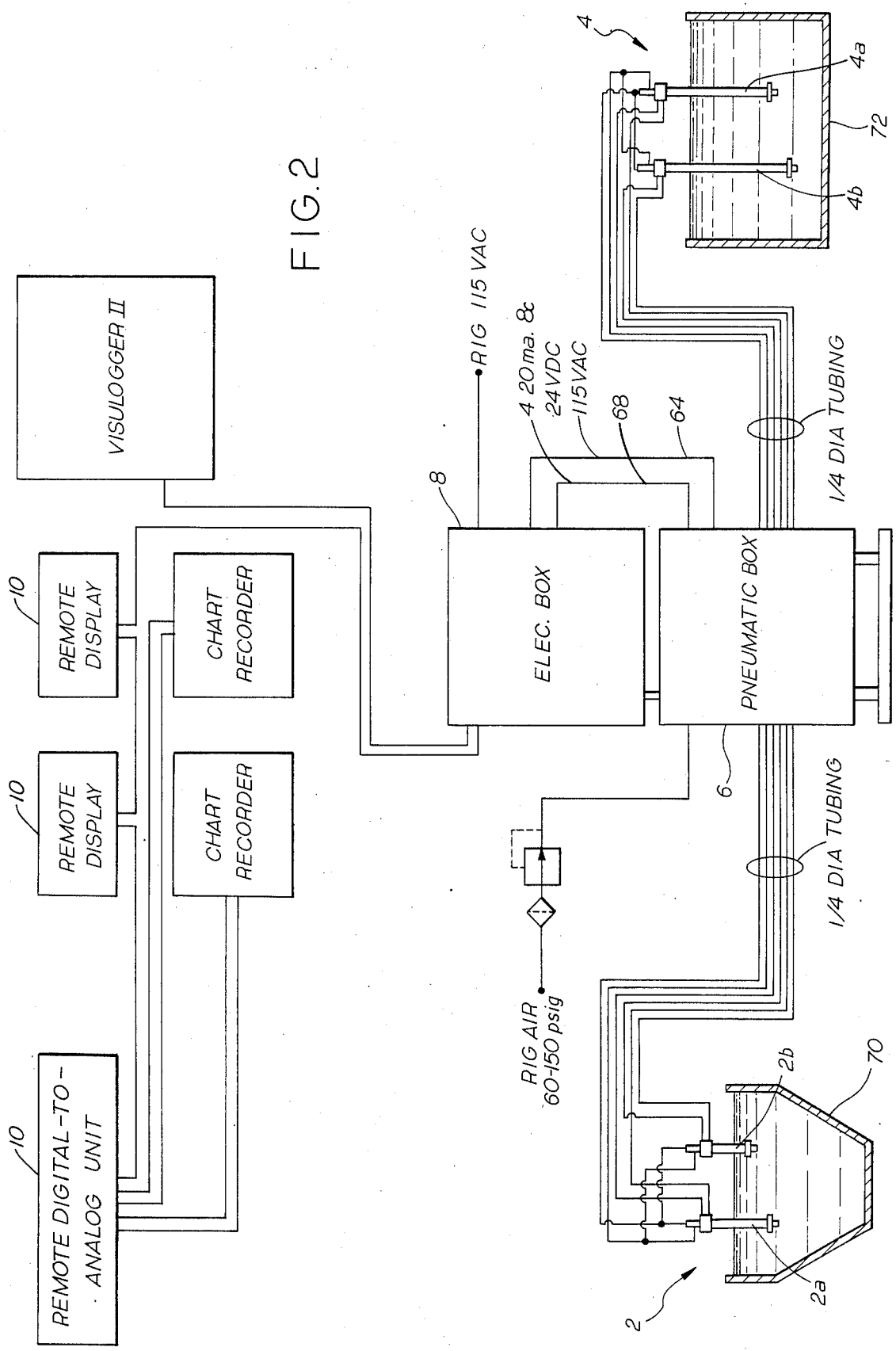
FIG. 2 is a view showing a configuration of the drilling fluid density measurement system and illustrating the interconnection of the subassembly comprising the entire system.

FIG. 2 shows the interconnection of the various subassemblies comprising the drilling fluid density measurement system. The preferred embodiment of this invention comprises a combination electrical and pneumatic system for measuring the density of fluid in two separate tanks 70 and 72, located at distinct points within a circulating drilling fluid system. It will, of course, be understood that this invention is suitable for use with a single tank or can be employed to measure the density of drilling fluid or drilling mud in a plurality of separate reservoirs or tanks. The pressure probe subassembly 2 and 4 disposed below the surface of drilling fluid contained in tanks 70 and 72 communicate with pneumatic box 6 by means of a plurality of pneumatic lines or tubing described in greater detail with reference to FIG. 3. In the preferred embodiment of this invention, these pneumatic lines can comprise conventional $\frac{1}{4}$-inch-diameter flexible tubing.

The pneumatic subassembly located within the pneumatic box 6 (FIG. 3) comprises a plurality of solenoid valves and a differential pressure transmitter 54 of conventional construction. Conventional flow regulators 30, 32, 34 and 36 communicating with the pressure probes 2 and 4, for delivering a gas to the pressure probes at selected flow rates, are also located within the penumatic subassembly 6. In the preferred embodiment of this invention, air is delivered to the pneumatic subassembly 6. from a standard rig air source at pressures ranging from 60 to 150 psi.

Electrical subassembly 8 is connected to the pneumatic subassembly 6 by means of conventional electrical cables 64 and 68 (FIG. 2). These cables are conventional in construction and comprise means for transmitting both power and signal currents to and from the pneumatic subassembly 6. Electrical subassembly 8 is in turn connected to one or more remote display units 10 which can be positioned at various locations on and around a drilling rig R. This drilling fluid density measurement system is especially adapted for use with a drilling monitoring system manufactured by Technical Oil Tool Company under the trademark "VISULOGGER".

The operation of the pneumatic subassembly of the drilling fluid density measurement system is described in greater detail in FIGS. 3 through 7. In each of these figures pneumatic lines transmitting pressure signals monitored in the configuration shown in the specific figure is depicted as a solid line. Dashed lines refer to pneumatic lines which are either disconnected or are not sensed for this specific operation in the figure. Note that the depiction of a pneumatic line as a dashed line in FIGS. 3 through 7 does not necessarily mean that the particular pneumatic line is disconnected or that the pressure in the line is equal to atmospheric or some other reference value.

Figure 3:
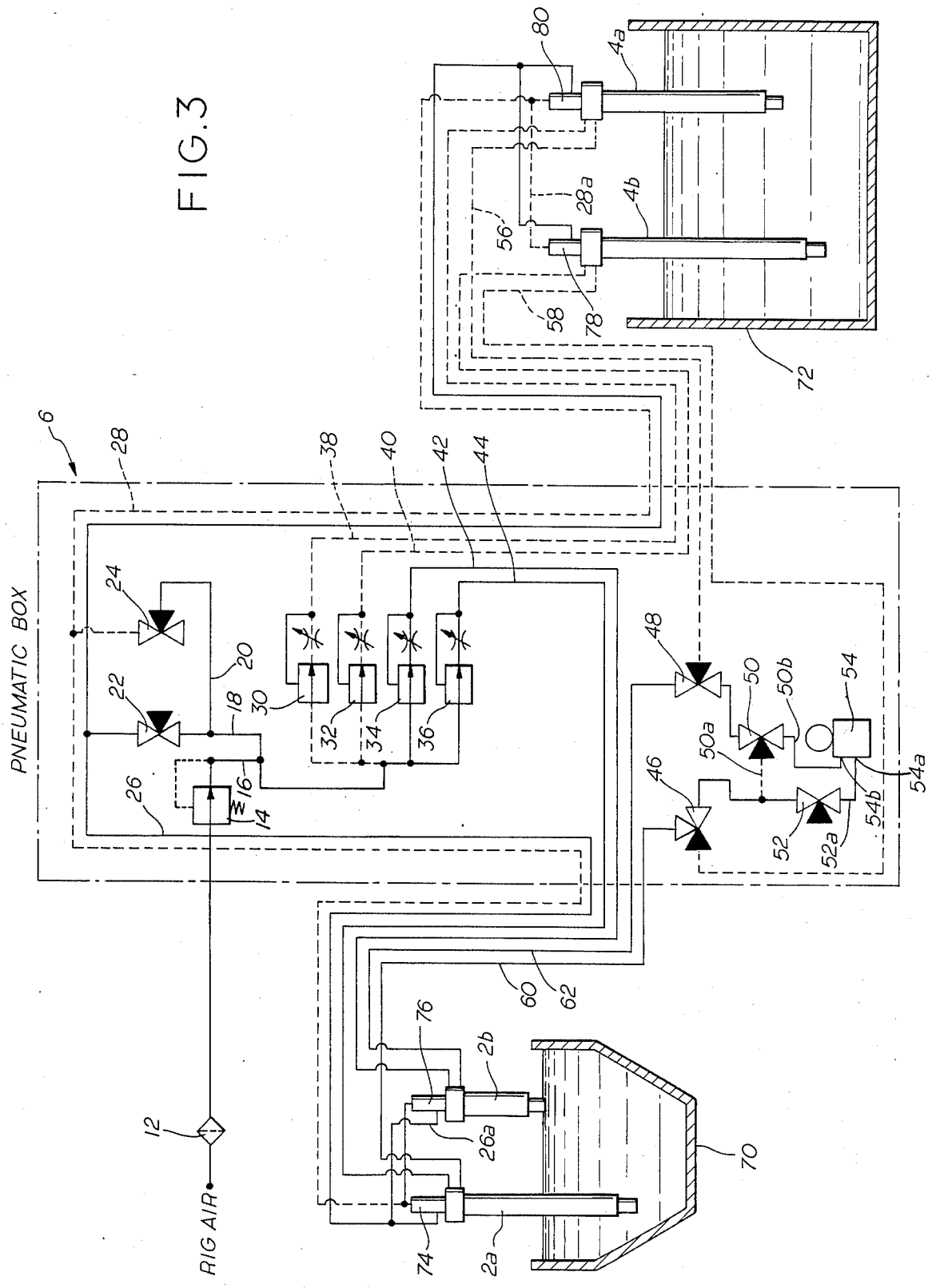
FIG. 3 is a view of the interconnection between the pneumatic pressure-sensing elements in the pneumatic box and the pressure probes located in reservoirs or tanks located adjacent the entrance of the drilling fluid into the well bore and adjacent the exit of the drilling fluid from the well bore.

FIG. 3 shows the configuration of the pneumatic system for monitoring the density of the drilling fluid located in reservoir 70, commonly called a mud pit or possum belly, located adjacent or downstream of the exit of the drilling fluid from the well bore in a circulating drilling fluid system. The various components of the pneumatic system will be described with reference to FIG. 3. The operation of the components in the various configurations of the pneumatic system will then be described in greater detail with reference to FIGS. 3 through 7.

A conventional pneumatic coupling 12 provides the means of interconnecting the pneumatic system with rig air available on conventional drilling rigs. This rig air is delivered first to a flow regulator 14 in pneumatic box 6 and then through a line 16 to the principal components of the pneumatic subassembly 6. It should be noted that this system is not limited to use with rig air or is indeed not limited to use of air. Any gas could theoretically be employed. Of course, only a non-combustible gas would be used. Incoming flow line 16 in turn communicates with four conventional flow regulators 30, 32, 34, and 36, positioned in parallel relationship. Each of the flow regulators 30, 32, 34, and 36 comprises means for regulating the flow of air or of some other gas to the pressure probes submerged in the drilling fluid in reservoirs 70 and 72. Air or gas is delivered to the pressure probes at prescribed flow rates. In the preferred embodiment of this invention, the volumetric flow rate of air delivered to each of the pressure probes 2a, 2b, 4a, and 4b is the same. Flow regulator 30 delivers air or a suitable gas to upper pressure probe 4a located in reservoir 72 through pneumatic line 38. Flow regulator 32 similarly delivers air to the lower pressure probe 4b in reservoir 72 through tubing 40. Flow regulator 34 delivers a gas or air through pneumatic line 42 to upper pressure probe 2b located within reservoir 70. Flow regulator 36 is similarly connected to lower pressure probe 2a through pneumatic line 44. The air delivered to pressure probes 2a, 2b, 4a, and 4b through lines 38, 40, 42, and 44 is bubbled down through the probes to a location within the drilling fluid located within the respective reservoir. The pressure opposing introduction of the gas through the tubular pressure probes 2a, 2b, 4a, and 4b is, of course, dependent upon the hydrostatic pressure at the point at which the gas or air is introduced into the fluid. As will be discussed with reference to FIG. 8, this pressure-opposing introduction of the gas into the fluid is sensed by the pressure probe and is communicated by a plurality of pneumatic lines to a differential pressure transmitter 54 located within the pneumatic box and comprising a part of the pneumatic subassembly 6. Pneumatic line 60 establishes communication with pressure probe 2a, while pneumatic line 62 separately communicates with upper pressure probe 2b in reservoir 70. Pneumatic line 56 is connected to upper pressure probe 4a and pneumatic line 58 is connected to lower pressure probe 4b in reservoir 72.

Four conventional solenoid valves 46, 48, 50, and 52 are located within the pneumatic box of the pneumatic subassembly 6 in communication with the pressure-sensing lines 56, 58, 60, and 62. Each of these solenoid valves comprise conventional valves. As depicted in FIGS. 3 through 7, the closed port on the valve is represented by a solid symbol while the open ports are represented by an open triangular symbol. Pressure is readily communicated between those portions of the solenoid valve which are open.

The differential pressure transmitter comprises a conventional device manufactured by Statham Div. of SCHLUMBERGER, INC. of Irvine, Calif., for use in converting a pneumatic pressure signal to an electrical signal. The differential pressure transmitter 54 has high and low pressure inputs. The high-pressure input 54a of the differential pressure transmitter communicates through line 52a with solenoid valve 52. The low-pressure input 54b of the differential pressure transmitter communicates through line 50b with solenoid valve 50. Thus, the pressure transmitted to the inputs 54a and 54b must proceed through solenoid valves 52 and 50, respectively.

Valve 52 in turn communicates with a first select stop valve 46 which is selectively communicable with pneumatic lines 58 and 60 which are connected to the lower pressure probes 2a and 4b. Since the lower pressure probes 2a and 4b will measure a higher fluid pressure than probes 2b and 4a, these pressure probes are positioned to selectively communicate with the high-pressure input 54a of the differential pressure controller 54 through stop valve 46 and solenoid valve 52. The pressure-sensing lines 56 and 62, communicable with upper pressure probes 2b and 4a, are in turn connected to a second stop valve 48. The output of stop valve 48 is communicable with solenoid valve 50 which is in turn communicable with the low-pressure input 54b to the differential pressure transmitter 54.

Figure 4:
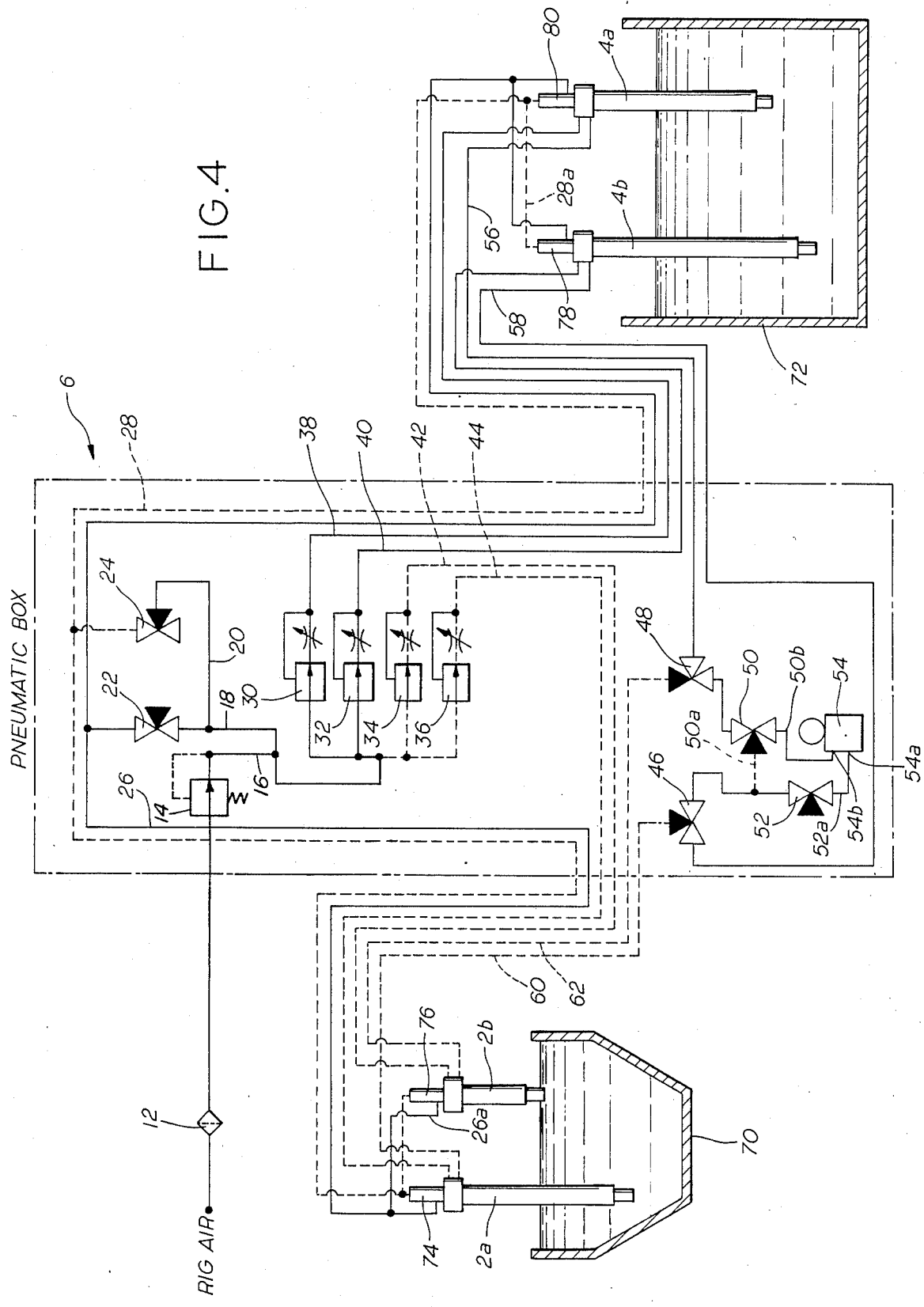
FIG. 4 is a view similar to FIG. 3 but showing the selective measurement of the density of the drilling fluid in the reservoir adjacent the entrance of the drilling fluid in the well bore.

As will be apparent with reference to FIGS. 3 and 4, stop valves 46 and 48 are simultaneously shiftable between two positions, one (FIG. 3) in which the pressure sensed by probes 2a and 2b opposing introduction of gas into the drilling fluid is sensed by the inputs 54a and 54b, respectively, of the differential pressure transmitter. In the other position (FIG. 4) of stop valves 46 and 48, the pressure sensed by pressure probes 4a and 4b through lines 56 and 58 is sensed by the differential pressure transmitter 54. In the configuration of FIG. 3, the pressure sensed by probes 2a and 2b is sensed by the differential pressure transmitter 54 as indicated by the solid lines. Both valves 52 and 50 remain open to the input from valves 46 and 48 as the pressure is sensed selectively in reservoir 70 and 72.

In addition to providing air or a gas to pressure probes 2a, 2b, 4a, and 4b through flow regulators 30, 32, 34, and 36, the input line 16 from the rig air supply also communicates through line 18 with solenoid valves 22 and 24. Pneumatic line 18 is communicable with solenoid valve 22 and with a pneumatic line 20 which is in turn in communication with solenoid valve 24 located in parallel with solenoid valve 22. As shown in FIG. 3, solenoid valve 22 is open and solenoid valve 24 is closed to air pressure supplied through line 20. The output of solenoid valve 22 supplies pressures through line 26 to actuator assemblies 74, 76, 78, and 80. These actuator assemblies comprise differential pressure actuators for rapidly shifting a self-cleaning member within pressure probes 2a, 2b, 4a, and 4b and will be described in more detail in connection with FIG. 8. Pressure supplied through line 26 maintains the actuators in their upper position to disengage the self cleaning device and permit normal operation of pressure probes 2a, 2b, 4a, and 4b. The operation of the self-cleaning pressure probes will be described in greater detail in connection with the description of FIG. 8.

Figure 5:
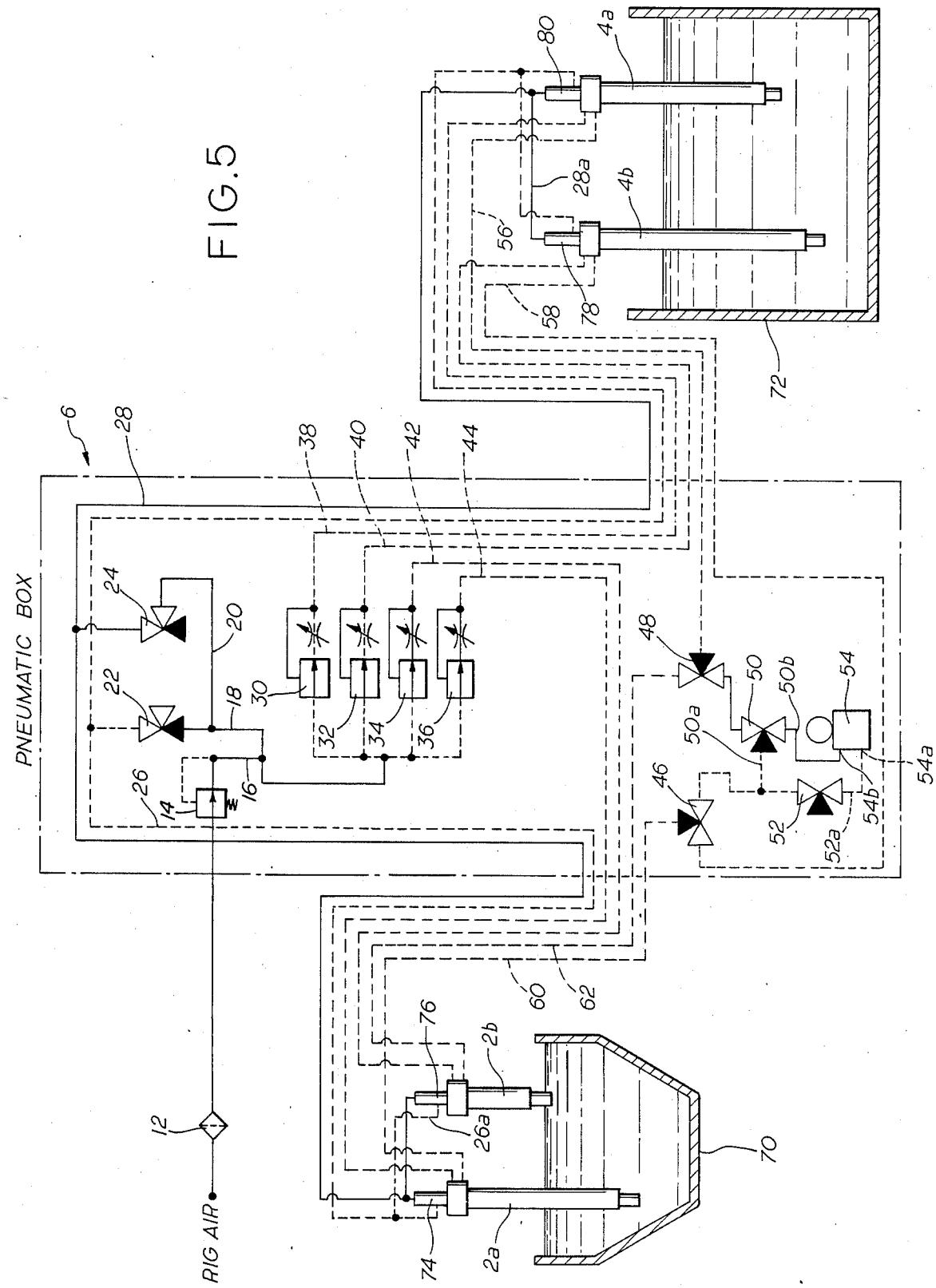
FIG. 5 is a view showing the actuation of a self-cleaning device to prevent clogging of the pressure probes by congealed drilling fluid.

Line 28 also communicates with differential pressure actuators 74, 76, 78, and 80 on each pressure probe. Line 28 in turn communicates with solenoid valve 24. In configuration of FIG. 3, solenoid valve 24 is vented to atmosphere, and line 28 is maintaining atmospheric pressure. When valve 24 is actuated to establish communication between line 20 and line 28, solenoid valve 22 is simultaneously actuated through vent line 26 to atmosphere. Thus, the pressure acting on differential actuators 74, 76, 78, and 80 is reversed for actuating this self-cleaning mechanism, as shown in FIG. 5.

FIG. 4 shows the configuration of the pneumatic system for measuring the density in reservoir 72. The configuration of the components in FIG. 4 is identical to the configuration in FIG. 3, but stop valves 46 and 48 have been shifted to establish communication between lower pressure probe 4b and the high-pressure input of differential pressure transmitter 54 and to establish communication between upper pressure probe 4a and the low-pressure input of differential pressure transmitter 54. Solenoid valves 22, 24, 50, and 52 remain in the same position as shown in FIG. 3.

Figure 6:
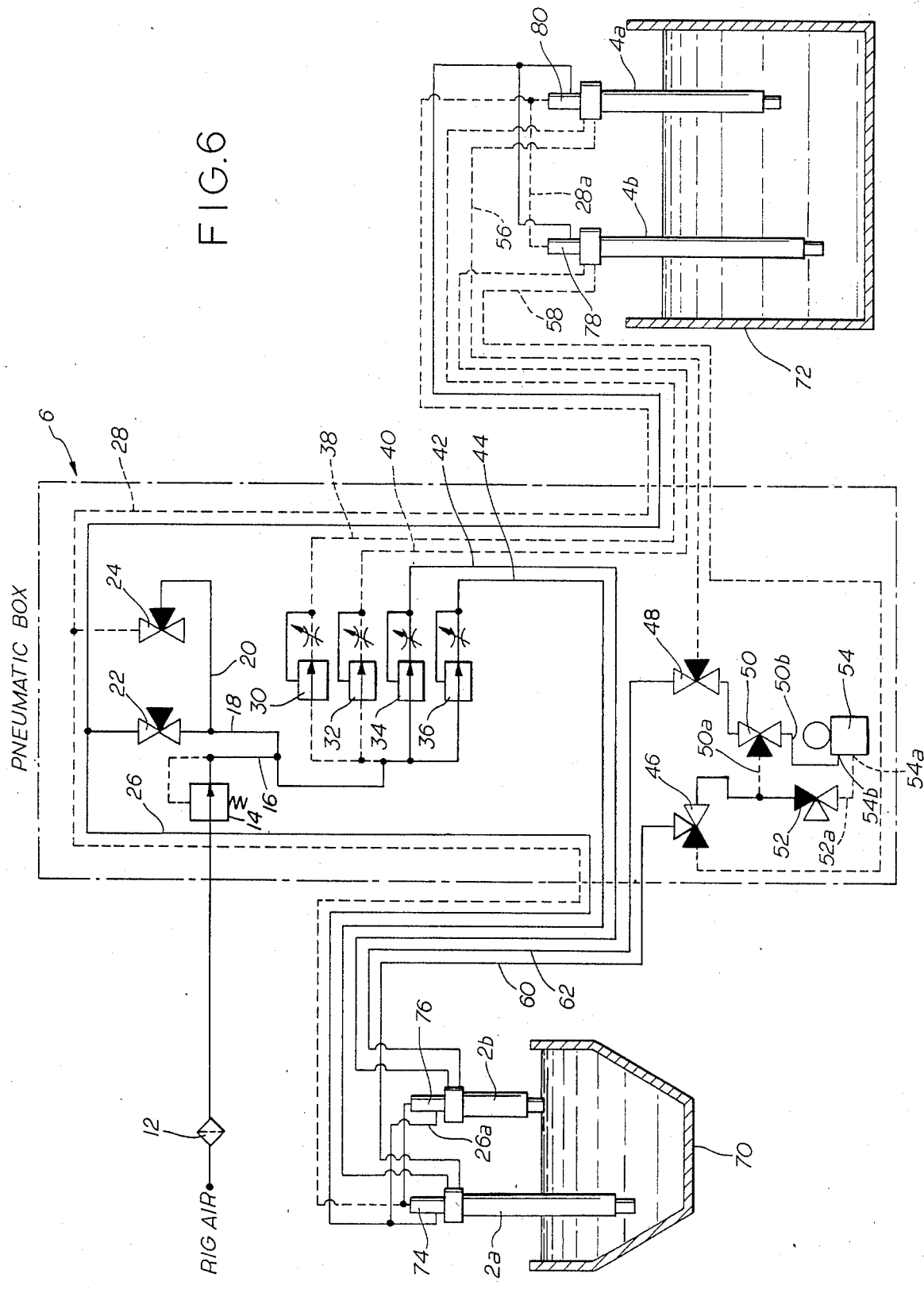
FIG. 6 is a view similar to FIG. 3 showing actuation of a level check device to determine if the pressure probes are submerged in one of the reservoirs.

FIG. 6 illustrates a configuration in which the level of the drilling fluid in reservoir 70 is checked to determine if the pressure probes 2a and 2b are both submerged within the drilling fluid. Only if the pressure probes 2a and 2b are submerged will the output of differential pressure transmitter 54 be related to the density of the fluid in reservoir 70. The level check apparatus comprises a level check solenoid valve 52 communicating with the high-pressure input 54a of the differential pressure transmitter 54. During the normal measuring configurations depicted in FIGS. 3 and 4, the level check valve 52 is open to the pressure sensed by the lower probes, either 2a or 4b, through stop valve 46. In the configuration of FIG. 6 the level check valve 52 is shifted from an open position, shown in FIGS. 3 and 4 to closed position to vent the high-pressure input 54a to atmospheric. If the upper pressure 2b shown in FIG. 6 is submerged, the pressure sensed at the low-pressure input 54b through valve 48 and line 62 will be greater than atmospheric. Thus, a negative pressure differential will be sensed by the differential pressure transmitter 54. Level-indicating means are provided in a microprocessor for interpreting a negative pressure signal, in the configuration of FIG. 6, to mean that the upper pressure probe 2b and the lower pressure probe 2a are both submerged. If the level of the drilling fluid in reservoir 70 were lowered to expose upper pressure probe 2b to atmospheric pressure, the pressure sensed by the low-pressure input 54b would be atmospheric. Since the high-pressure input 54a also senses atmospheric pressure in the configuration of FIG. 6, the differential pressure across the differential pressure transmitter 54 would be equal to zero. A level-indicating means contained within the microprocessor would interpret a zero differential pressure output by differential pressure transmitter 54 in configuration of FIG. 6 to mean that one or both of the pressure probes 2a or 2b is not submerged and that the differential pressure signal is not related to the density of the fluid in reservoir 70. The level check system depicted in FIG. 6 could be employed in the same manner for determining the level of the drilling fluid in reservoir 72.

Figure 7:
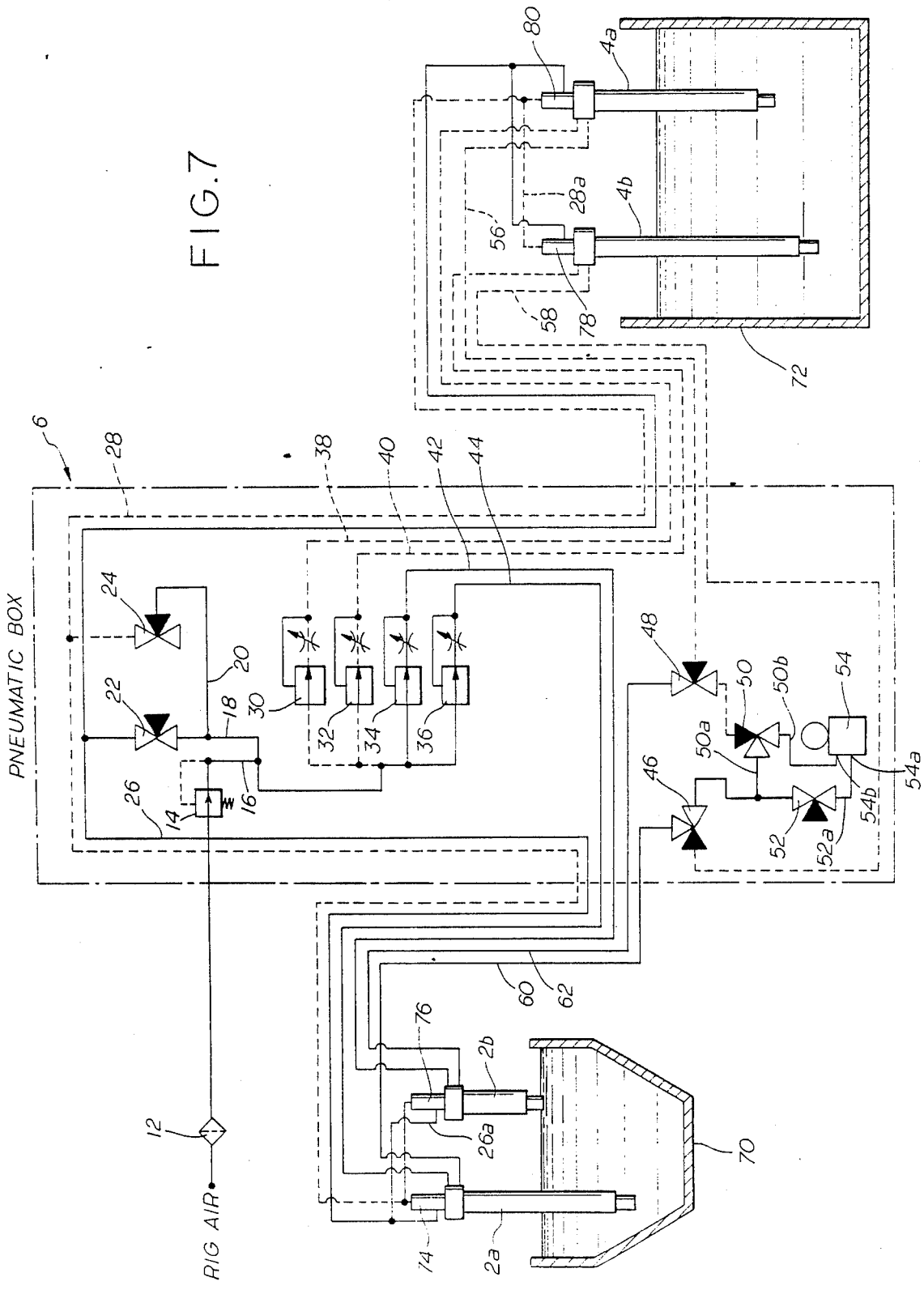
FIG. 7 is a view of the configuration of the pneumatic system for intermittently redetermining the level of the output signal from a differential pressure transmitter corresponding to zero differential pressure.

FIG. 7 depicts a configuration in which the output corresponding to zero differential pressure across differential pressure transmitter 54 can be determined. The zeroing means comprises in part a shiftable valve 50 communicable with both the high- and low-pressure lines leading from select valves 46 and 48. When the shiftable zero valve 50 is in the open position shown in FIGS. 3 and 4, the low pressure sensed by upper probes 2b and 4a is transmitted to the low pressure input 54b of the differential pressure transmitter. In order to zero the differential pressure transmitter and account for any drift which can occur with time, the shiftable valve 50 is shifted from the first position shown in FIGS. 3 and 4 to a second position shown in FIG. 7. In the second position, the low-pressure input 54b of the differential pressure transmitter 54 is connected to the high-pressure signal through select valve 46 through line 50a. Since the high-pressure signal through select valve 46 is now sensed by both the high-pressure input 54a and the low-pressure input 54b of the differential pressure transmitter 54, the differential pressure existing thereacross is equal to zero. Thus, the signal transmitted by the differential pressure transmitter in this configuration can be correlated by the microprocessor to an output signal correlating to zero differential pressure. Subsequent pressure measurements by probes 2a, 2b, 4a, and 4b can then be correlated to this zero pressure differential reference signal to eliminate any drift at the zero signal and maintain an accurate measurement of differential pressure and drilling fluid density. Both the level check valve 52 and the zero valve 50 can be intermittently regulated and actuated by the microprocessor for continuous operation of the apparatus. The microprocessor also correlates the differential pressure output signal to the density of the drilling fluid in the reservoir.

Figure 8:
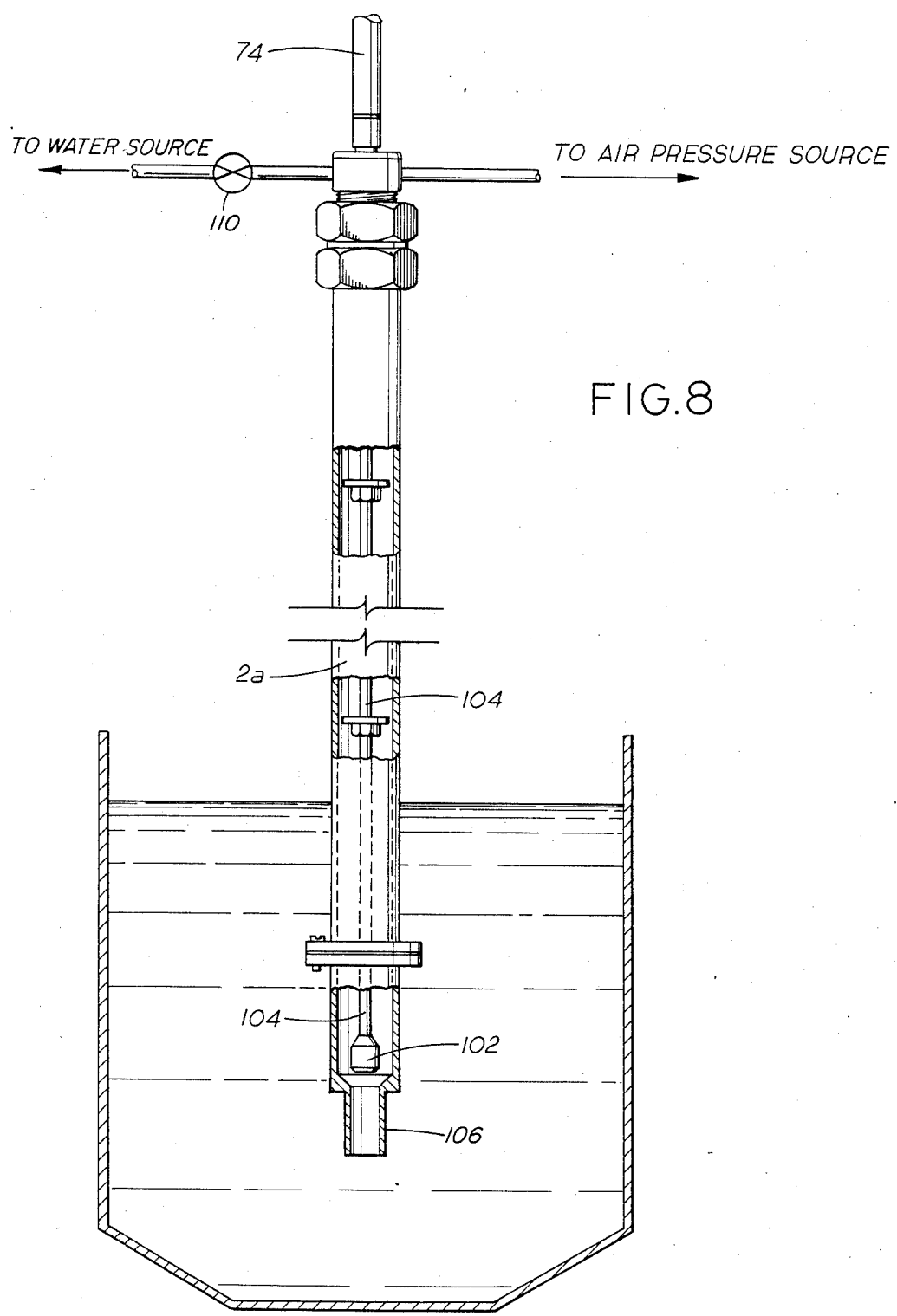
FIG. 8 is a schematic view of one of the self cleaning pressure probes employed in the preferred embodiment of this invention.

FIG. 8 depicts the operation of the self cleaning mechanism for the tubular pressure probes 2a, 2b, 4a, and 4b. Each of these tubular pressure probes is equipped with a preferred embodiment of this invention. This self-cleaning mechanism is described in greater detail in U.S. patent application No. 919,010, filed Oct. 15, 1986. These self-cleaning mechanisms are used to prevent the drilling fluid from clogging the exit or nozzle of each of the tubular probes. This clogging problem is aggravated in a drilling fluid measurement system, since one of the properties of a suitable drilling fluid is the ability to clog or stop up crevices and pores which may be encountered within the well bore. Periodic cleaning is therefore necessary to insure that the tubular pressure probes 2a, 2b, 4a, and 4b do not become clogged. In the preferred embodiment of this invention, the self-cleaning mechanism comprises a cleaning plunger 102 positioned on the end of a rod 104 which traverses the length of the tubular pressure probe 2a in FIG. 8, and connected at the upper end to actuator 74. The cleaning plunger is only slightly smaller in diameter than the axial passageway defined by a nozzle 106 at the end of the tubular probe 2a, and hence, when the cleaning plunger is disposed in its inactive position within the larger diameter bore of the tubular probe 2a, it offers no impediment to the flow of air through the probe tube. Periodically the actuating mechanism is energized, by applied pressure as described in reference to FIG. 5, to effect a rapid reciprocation of the cleaning plunger 102 through the nozzle at the end of the probe. Any drilling fluid or mud which has congealed at the nozzle or free end of the probe 2a is thus freed by movement of the cleaning plunger 102 therethrough. When the cleaning plunger is withdrawn into the bore of the tubular probe 2a to its inoperative position, the plunger is cleaned and does not restrict the flow of air or gas there-cleaned and does not restrict the flow of air or gas therethrough. Identical cleaning apparatus is provided for probes 2b, 4a and 4b.

If the particular mud tends to congeal or cake sufficiently to block the passage of cleaning plunger 102 through nozzle 106, it is desirable to inject a small quantity of water into nozzle 106. Such injection may be conveniently accomplished by a pneumatic valve 110 (FIG. 8) which is briefly opened by being connected in parallel with actuator 74 to line 26. Similar water injection valves (not shown) are connected to probes 2b, 4a and 4b and are actuated concurrently with plunger actuators 76, 78 and 80.

What is claimed and desired to be secured by Letters Patent is:

1. An apparatus for measuring the density of a drilling fluid within a reservoir at the surface of a well, the drilling fluid being circulated through the subterranean well bore during drilling thereof, the circulation path of the drilling fluid including the reservoir; the apparatus comprising: first and second tubular means continuously disposed in the reservoir, each for introducing a gas at different depths within the drilling fluid in the reservoir; flow-regulating means for delivering the gas to the first and second tubular means at selected flow rates; a differential pressure transmitter; pneumatic means for communicating the pressure-opposing introduction of the gas into the drilling fluid from the first and second tubular means to the differential pressure transmitter, the differential pressure transmitter comprising means for emitting an output signal related to the difference in pressure opposing introduction of the gas at the first and second tubular means; zeroing means for intermittently determining a value of the differential pressure transmitter output signal corresponding to zero differential pressure; level check means for intermittently determining if the level of the drilling fluid in the reservoir is above the first and second tubular means; and microprocessor means for regulating the zeroing means and the level check means and for correlating the differential pressure transmitter output signal to the density of the drilling fluid in the reservoir.

2. The apparatus of claim 1 wherein the zeroing means comprises means for inputing the pressure in one of the first or second tubular means simultaneously into the differential pressure transmitter whereby the differential pressure thereacross is zero and the simultaneous output of the differential pressure transmitter corresponds to the instantaneous zero value of the differential pressure transmitter output signal.

3. The apparatus of claim 2 wherein the zeroing means comprises valve means selectively communicable with the first and second tubular means.

4. The apparatus of claim 1 wherein the level check means comprises valve means communicable with one of the first or second tubular means in which the pressure opposing introduction of the gas into the drilling fluid is higher than the pressure of the gas in said first or second tubular means and with a corresponding input on the differential pressure transmitter, the valve means being selectively actuable for reducing the pressure at the corresponding input on the differential pressure transmitter to atmospheric, whereby a negative differential pressure signal is sensed when the other of the first and second tubular means is submerged in the drilling fluid, and the gas delivered therethrough is subjected to a pressure greater than atmospheric.

5. The apparatus of claim 4 wherein the one tubular means communicable with the valve means is the deeper of the first and second tubular means.

6. The apparatus of claim 1 further comprising an apparatus having first and second tubular means-simultaneously, continuously disposed in a plurality of separate reservoirs.

7. The apparatus of claim 6 wherein the tubular means in separate reservoirs are communicable with a single differential pressure transmitter.

8. The apparatus of claim 7 comprising selecting valves for alternatively establishing communication between tubular members in separate reservoirs and the single differential pressure transmitter.

9. The apparatus of claim 8 wherein the first and second tubular means are disposed in a first reservoir adjacent the exit of the drilling fluid from the well bore and separate first and second tubular means are disposed in a reservoir at the entrance of drilling fluids into the well bore.

10. The apparatus of claim 1 wherein the pneumatic means comprises tubing connecting the first and second tubular means to the differential pressure transmitter.

11. The apparatus of claim 1 further comprising self-cleaning means periodically operated by said microprocessor means for maintaining a clear passage through the first and second tubular means to prevent the drilling fluid from clogging the first and second tubular means.

12. The apparatus for measuring the density of a drilling fluid within a reservoir at the surface of a well, the drilling fluid being circulated throughthe subterranean well bore during drilling thereof; comprising: upper and lower pressure probes disposed at different depths in the drilling fluid in the reservoir and comprising means for introducing a gas into the drilling fluid at different depths; flow-regulating means for delivering the gas to the upper and lower pressure probes at prescribed flow rates; a differential pressure transmitter; pneumatic lines interconnecting the upper and lower pressure probes with separate inputs of a differential pressure transmitter and comprising means for communcating the pressure-opposing introduction of the gas into the drilling fluid from the upper and lower pressure probes to the differential pressure transmitter, the differential pressure transmitter comprising means emitting an output signal relatedto the difference in hydrostatic pressure due to the different depths of the upper and lower pressure probes in the drilling fluid; zeroing means for determining a value of the differential pressure transmitter output signal corresponding to zero differential pressure, the zeroing means including a valve disposed in communication with the pneumatic lines communicating with both the upper and lower pressure probes and with one input to the differential pressure transmitter, the valve being shiftable between first and second position; in the first position the upper and lower pressure probes communicating with separate inputs to the differential pressure transmitter, and in the second position one of the upper and lower pressure probes communicating with both inputs to the differential pressure transmitter and the other pressure probe communicating with neither of the differential pressure transmitter inputs, whereby the differential pressure sensed by the differential pressure transmitter is zero; and correlation means for correlating the differential pressure transmitter output signal to the density of the drilling fluid in the reservoir.

13. The apparatus of claim 12 wherein the correlation means comprises a microprocessor, the microprocessor also regulating intermittent actuation of the shiftable valve from the first to the second position.

14. An apparatus for measuring the density of a drilling fluid within a reservoir at the surface of the well, the drilling fluid being circulated through the subterranean well bore during drilling thereof; the apparatus comprising: upper and lower pressure probes disposed at different depths in the drilling fluid in the reservoir and comprising means for introducing a gas into the drilling fluid at different depths; flow-regulating means for delivering the gas to the upper and lower pressure probes at prescribed flow rates; a differential pressure transmitter; pneumatic lines interconnecting the upper and lower pressure probes with high-pressure and low-pressure inputs of a differential pressure transmitter and comprising means for communicating the pressure-opposing introduction of the gas into the drilling fluid from the upper and lower pressure probes to the differential pressure transmitter, the differential pressure transmitter comprising means for emitting an output signal related to the difference in hydrostatic pressure due to the different depths of the upper and lower pressure probes in the drilling fluid; level check means for determining if the level of the drilling fluid in the reservoir is above the upper and lower pressure probe, the level check means comprising a stop valve in the pneumatic line between the lower pressure probe and the high-pressure input to the differential pressure transmitter, the stop valve being shiftable between an open position in which the pressure sensed by the lower pressure probe is communicated with the high-pressure input and a closed position in which the high-pressure input senses atmospheric pressure, and level check means for indicating when the upper and lower pressure probes are submerged in drilling fluid, the level check means being responsive to a negative pressure signal from the differential pressure transmitter when the high-pressure input is exposed to atmospheric pressure and the submerged upper pressure probe is exposed to a pressure greater than atmospheric, to indicate that the pressure probes are submerged and responsive to a zero pressure signal when the upper pressure probe is not submerged and is exposed to atmospheric pressure, to indicate that the level of the drilling fluid is below the upper pressure probe, whereby the output signal from the differential pressure transmitter, when the valve is in the one position is not related to the density of the drilling fluid.

15. The apparatus of claim 14 wherein the level check means further comprises a microprocessor, the microprocessor also regualating intermittent actuation of the stop valve from the open to the closed position.

* * * * *